US005830169A

United States Patent [19]

Pierce

[11] Patent Number: 5,830,169

[45] Date of Patent: Nov. 3, 1998

[54] SPINE RELAXING APPARATUS

[76] Inventor: Charles W. Pierce, Hurricane Harbor #1 47 St. Gulf, Marathon, Fla. 33050

[21] Appl. No.: 858,584

[22] Filed: May 19, 1997

[51] Int. Cl.$^{6}$ .......... A61F 5/00

[52] U.S. Cl. .......... 602/32; 602/36

[58] Field of Search .......... 602/19, 32–36, 602/38, 40; 128/845; 606/240, 241, 242; 482/143, 144; 601/97, 98, 101

[56] References Cited

U.S. PATENT DOCUMENTS

| | | | |
|---|---|---|---|
| 3,752,153 | 8/1973 | Copeland | 606/242 X |
| 3,871,366 | 3/1975 | Cotrel | 602/33 |
| 4,207,879 | 6/1980 | Sofadago et al. | 606/242 |
| 4,583,532 | 4/1986 | Jones | 602/32 |
| 4,890,604 | 1/1990 | Nelson | 602/32 |
| 5,462,518 | 10/1995 | Hatley et al. | 602/36 |
| 5,575,765 | 11/1996 | Foster | 602/32 |

*Primary Examiner*—Linda C. Dvorak
*Assistant Examiner*—Denise Pothier
*Attorney, Agent, or Firm*—Haynes and Boone; James R. Bell

[57] ABSTRACT

A spine relaxing device includes a base and a support column vertically supported on the base. An adjustable main support member, an adjustable head support member and an adjustable foot support member are mounted on the support column. The head and foot members are movable relative to each other support member. A hand operated control device can be operated by the user to move the position of the head support member and the foot support member relative to the main support member. The main support member and head support member are adjustable in width.

17 Claims, 3 Drawing Sheets

SPINE RELAXING APPARATUS

BACKGROUND OF THE INVENTION

This invention relates generally to a spine relaxing apparatus and more particularly to a device having relatively adjustable supports for relieving compression on the spine.

Various devices have been proposed for the purpose of relaxing the spine of the body of a human. One such approach discloses a device for decompressing the spine using an elongated adjustable strap and a pad secured to the strap. The pad and strap assembly is placed in engagement with the body in the vicinity of the lower back. A portion of the strap is adjustable to extend to a portion of the body below the knees or around the feet. The user can then flex their knees or feet thereby placing traction on the spine at the lower back.

Another device stretches and strengthens the muscles of the lower back and legs of the user. This device includes a backboard and a belt to restrain the user's pelvis. A simple cable is provided with sliding handles, a pulley guiding system and leg supporting slings. For stretching the spine, the handles are slowly pulled by the user to raise the legs, thereby stretching the support muscles of the spine.

A further device has been provided for applying continuously variable suspension, traction and decompressive forces to the spine. This device utilizes spring loaded tube assemblies which extend from underarm supports which also have handles interconnected to the supports by means of straps. The spring loaded tubes apply an upward force under the arms which raises the shoulders to induce traction on the spine. Exercise is accomplished by repeatedly forcing the shoulders down against the biasing force and then allowing the biasing means to raise the shoulders.

Therefore, what is needed is a spine relaxing apparatus having relatively adjustable supports for relieving compression selectively on the upper and lower portions of the spine in a manner in which the user can relax and not be required to exert forces applied by using other parts of the user's body.

SUMMARY OF THE INVENTION

The present invention, accordingly, provides an apparatus for relieving compression on the spine by means of relatively adjustable support members. To this end, a spine relaxing apparatus includes a support column and a main support member mounted on the column. A head support member and a foot support member are movably mounted on the support column and are movably mounted relative to each other support member.

DESCRIPTION OF THE PREFERRED EMBODIMENT

Figure 1:
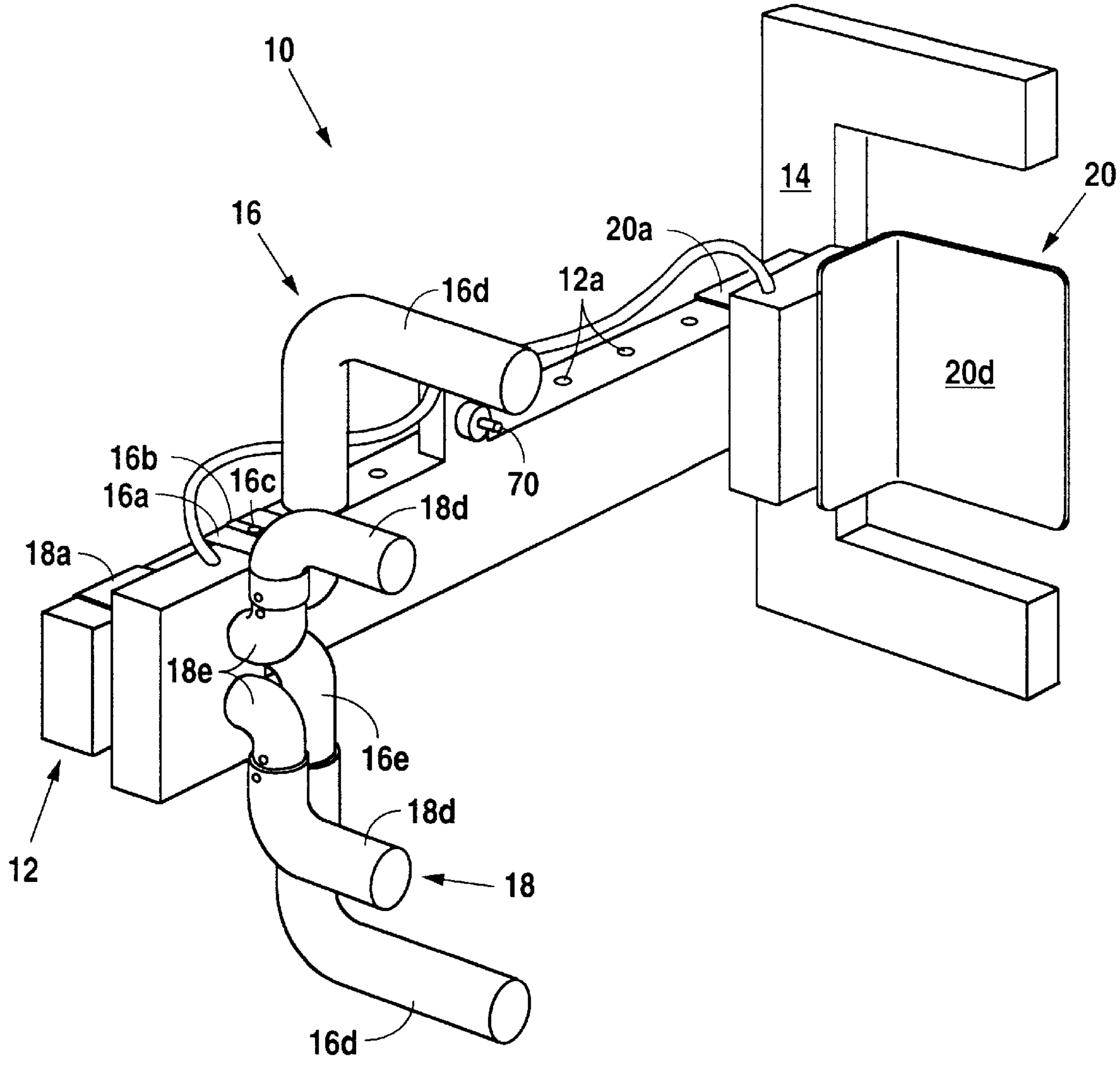
FIG. 1 is an isometric view illustrating an embodiment of the spine relaxing apparatus disclosed herein.

A spine relaxing apparatus is generally designated 10 in FIG. 1 and includes a support column 12, supported by and extending vertically from a base 14. A main support member 16 is mounted on column 12 and is adjustably positionable relative thereto. A head support member 18 is adjustably positionable and moveably mounted on column 12 as is a foot support member 20. As such, the main support member 16, head support member 18 and foot support member 20 are each positionable on support column 12. Head support 18 and foot support 20 are also movable relative to each other and relative to main support member 16 after positioning. As a result, the apparatus 10 is vertically adjustable to accommodate various body heights.

Figure 2:
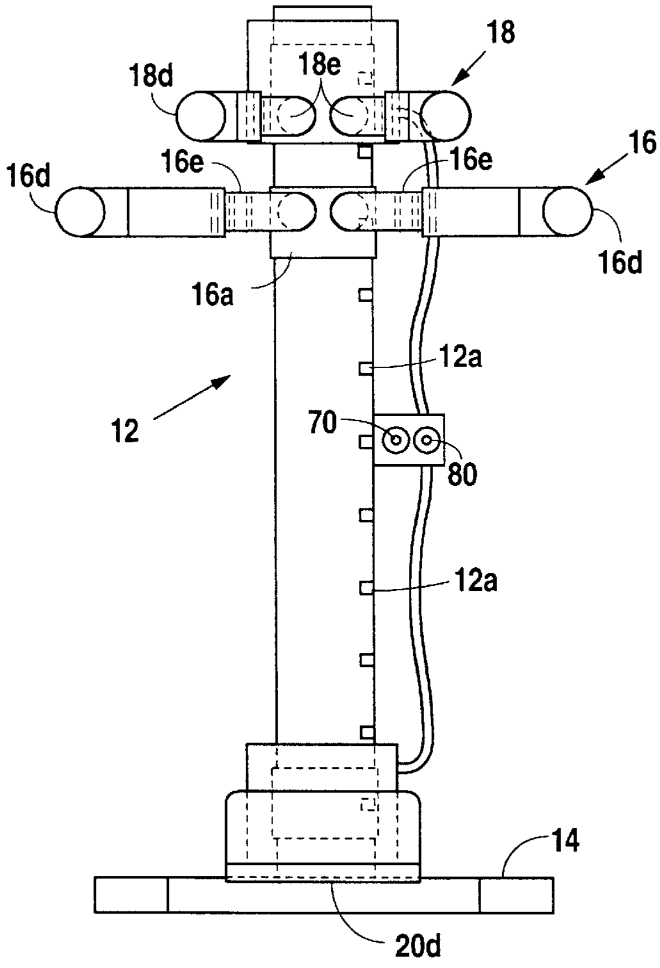
FIG. 2 is a frontal view illustrating an embodiment of the spine relaxing apparatus.
Figure 3:
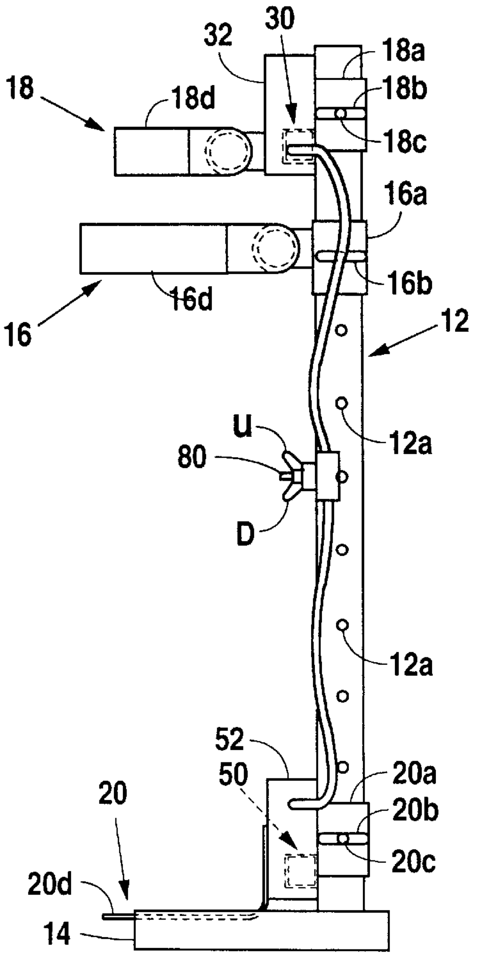
FIG. 3 is a side view illustrating an embodiment of the spine relaxing apparatus.

Main support member 16, FIGS. 1–3, is vertically positionable on column 12 by means of a sleeve 16*a* which is attached to member 16 and which slidably engages column 12. Also, a key 16*b* is insertable through an aperture 16*c* in sleeve 16*a* when in alignment with one of the apertures 12*a* in column 12. In addition, a pair of padded portions 16*d* of main support 16 are provided to support some of the users body weight when the user assumes a position on apparatus 10 whereby padded portions 16*d* are engaged with the users underarms, or armpits. Furthermore, padded portions 16*d* are telescopingly mounted on receiver portions 16*e* so that main support member 16 is width adjustable to accommodate various body widths.

Head support member 18, FIGS. 1–3, is vertically positionable on column 12 by means of a sleeve 18*a* which is attached to member 18 and which sidably engages column 12. Also, a key 18*b* is insertable through an aperture 18*c* in sleeve 18*a* when in alignment with one of the apertures 12*a* in column 12. In addition, a pair of padded portions 18*d* of head support portion 16 are provided to support the users head when the user assumes a position on apparatus 10 whereby the users body weight is supported by means of padded portions 16*d* being engaged with the users underarms. Padded portions 18*d* are simultaneously engaged beneath the jaws of the users head. Furthermore, padded portions 18*d* are telescopingly mounted on receiver portions 18*e* so that support member 18 is width adjustable to accommodate various head widths.

Foot support member 20, FIGS. 1–3, is vertically positionable in column 12 by means of a sleeve 20*a* which is attached to member 20 and which slidably engages column 12. Also, a key 20*b* is insertable through an aperture 20*c* in sleeve 20*a* when in alignment with one of the apertures 12*a* in column 12. Foot support member 20 supports some of the users body weight when the users feet are positioned on a foot rest portion 20*d* of member 20.

As described above, major or coarse adjustments are achievable to adapt the support members 16, 18 and 20 to the user's physical characteristics as closely as possible. After the major adjustments are achieved, minor adjustments to the foot support 20 and head support 18 can be made within limits in a manner discussed below, to relax and relieve compression on the users neck and back.

Once the above-described major or coarse adjustments have been made, as described above, fine adjustments may be made to head support member 18 and foot support member 20 as will be discussed below.

Figure 4:
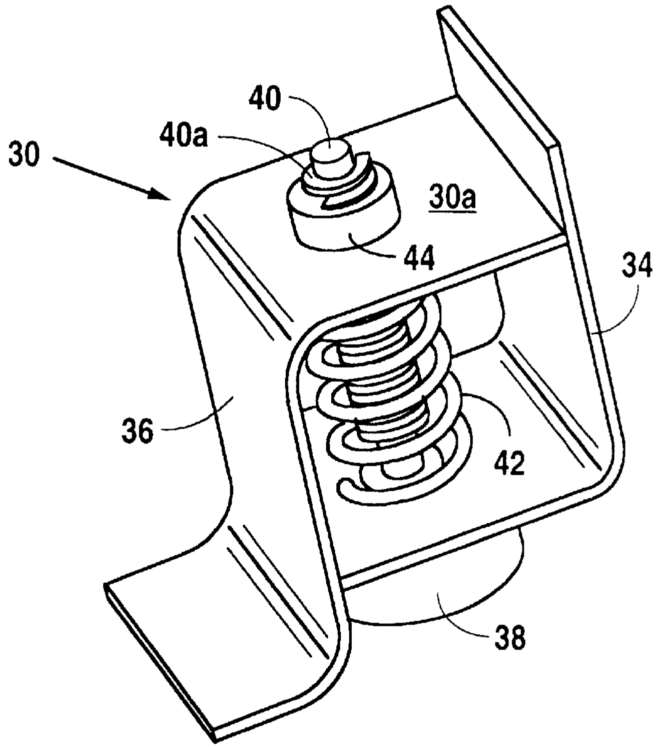
FIG. 4 is an isometric view illustrating an embodiment of a screw adjustment device used with the spine relaxing apparatus disclosed herein.

Head support member 18 is mounted for movement relative to sleeve 18*a* by an actuator 30, FIGS. 3 and 4. Actuator 30 is mounted in a protective cover 32, FIG. 3, and includes a first plate 34, FIG. 4., fixedly attached to sleeve 18*a*, FIG. 3. A second plate 36, FIG. 4 is mounted for movement relative to first plate 34 and is connected to move head support member 18, FIG. 3, . The relative movement between plates 34 and 36 is accomplished by means of a commercially available DC motor 38, FIG. 4, mounted on plate 34 and connected to rotate a threaded 40 rod which extends freely through an opening in plate 36 so that threads 40*a* of rod 40 do not engage plate 36. A low-rate compression spring 42 is mounted between plates 34 and 36. Spring 42 is coaxially mounted with rod 40. Rod 40 is threadably received by a nut 44 non-rotatably mounted on an exterior surface 30*a* of actuator 30. Threads 40*a* are of a low pitch so that rotation of rod 40 moves plate 36 gradually relative to plate 34.

Figure 5:
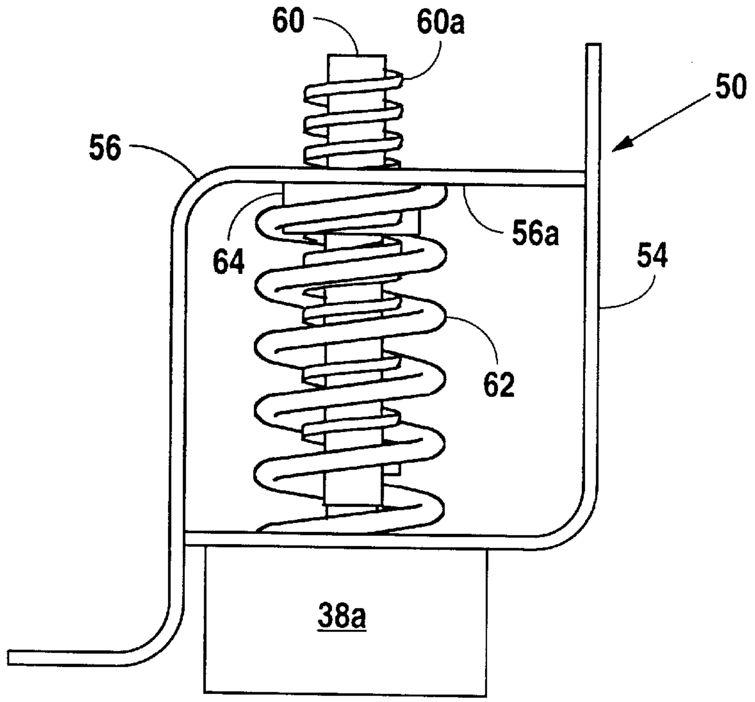
FIG. 5 is a side view illustrating an embodiment of the screw adjustment device.

Foot support member 20 is mounted for movement relative to sleeve 20*a* by an actuator 50, FIGS. 3 and 5. Actuator 50 is mounted in a protective cover 52, FIG. 3, and includes a first plate 54, FIG. 5, fixedly attached to sleeve 20*a*, FIG. 3. A second plate 56, FIG. 5, is mounted for movement relative to first plate 54 and is connected to move foot support member 20, FIG. 3. The relative movement between plates 54 and 56, FIG. 5, is accomplished by means of a commercially available motor 38*a*, similar to motor 38 discussed above, mounted on plate 54 and connected to rotate a threaded rod 60 which extends freely through an opening in plate 56 so that threads 60*a* of rod 60 do not engage plate 56. A low rate compression spring 62 is mounted between plates 54 and 56. Spring 62 is coaxially mounted with rod 60. Rod 60 is threadably received by a nut 64 non-rotatably mounted on an interior surface 56a of plate 56. Threads 60*a* are of a low pitch so that rotation of rod 60 moves plate 56 gradually relative to plate 54.

Motors 38, 38*a* are operably connected to three-position toggle-type switches 70 and 80, FIGS. 1–3, which function similarly. One of the positions "U", i.e. an up position, moves the respective support 18 or 20 in the upward direction by rotating the respective threaded rod in a first direction. Another position, i.e. a down position, "D" moves the respective support 18 or 20 in the downward direction by rotating the respective threaded rod in a second direction opposite the first direction. A third position, i.e. a neutral position, between the up and down position, maintains the respective support 18 or 20 stationary due to non-rotation of the respective threaded rod.

In operation, when it is desired to use the spine relaxing apparatus 10, the head support 18, main support 16 and foot support 20 are adjusted to accommodate the user's body height by sliding the respective sleeves 18*a*, 16*a*, 20*a* along column 12 and inserting the respective keys 18*b*, 16*b*, 20*b* in the appropriate apertures 12*a*. Width adjustments to main support 16 and head support 18 are made. The user then positions his or her body to stand on foot support 20 and permit main support padded portions 16*d* to support the underarms and padded portions 18*d* to support the head under the jaws. By manipulating toggle switches 70 and 80, fine adjustments to the head and foot supports are gradually accomplished to relieve spinal compression to the degree desired. It should be noted that the springs used and the thread pitch provided are such that only gradual limited adjustments and forces are permitted. For example, as it can be seen in FIG. 4, as motor 38 rotates screw 40 in a clockwise direction, compression of spring 42 becomes relaxed and therefore exerts an upward force proportional to the displacement. In FIG. 5, it can be seen that as screw 60 moves in a counterclockwise direction, the weight supported by plate 56 is transferred from screw 60 to spring 62, providing support proportional to the displacement of spring 62.

The use of these mechanisms, including the springs, provides a controlled means for gradually extending the spine while limiting the extension and forces induced by the apparatus.

Although illustrative embodiments of the invention have been shown and described, a wide range of modifications, change and substitution is contemplated in the foregoing disclosure and in some instances, some features of the present invention may be employed without a corresponding use of other features. Accordingly, it is appropriate that the appended claims be construed broadly and in a manner consistent with the scope of the invention.

What is claimed is:

1. A spine relaxing apparatus comprising:

a support column;

a main support member mounted on the support column; a head support member mounted on the support column and being manually incrementally adjustable relative to the main support member and being further adjustable relative to the main support member by a first motorized actuator; and a foot support member mounted on the support column and being manually incrementally adjustable relative to the main support member and being further adjustable relative to the main support member by a second motorized actuator.

2. The apparatus as defined in claim 1 further comprising a base, the support column being supported by the base.

3. The apparatus as defined in claim 2 wherein the main support member is adjustably mounted on the support column.

4. The apparatus as defined in claim 1 wherein the head support member is width adjustable.

5. The apparatus as defined in claim 4 wherein the main support member is width adjustable.

6. The apparatus as defined in claim 1 wherein the head support member is movable toward and away from the main support member.

7. The apparatus as defined in claim 6 wherein the foot support member is movable toward and away from the main support member.

8. A spine relaxing apparatus comprising:

a base;

a support column supported on the base; a main support member mounted on the support column, the main support member being manually incrementally adjustable relative to the support column;

a head support member mounted on the support column and being manually incrementally adjustable relative to the main support member, and being further adjustable relative to the main support member by a first motorized actuator; and a foot support member mounted on the support column and being manually incrementally adjustable relative to the main support member, and being further adjustable relative to the main support member by a second motorized actuator.

9. The apparatus as defined in claim 8 wherein the head support member is width adjustable.

10. The apparatus as defined in claim 9 wherein the main support member is width adjustable.

11. The apparatus as defined in claim 8 wherein the head support member is movable toward and away from the main support member.

12. The apparatus as defined in claim 11 wherein the foot support member is movable toward and away from the main support member.

13. A spine relaxing apparatus comprising:

a base;

a support column supported on the base; an adjustable main support member, an adjustable head support member and an adjustable foot support member;

the main support member being mounted on the support column and being manually incrementally adjustable relative to the main support column;

the head support member mounted on the support column and being manually incrementally adjustable relative to the main support member, and being further adjustable relative to the main support member and the foot support member by a motorized actuator; and the foot support member mounted on the support column and being manually incrementally adjustable relative to the main support member and the head support member, and being further adjustable relative.

14. The apparatus as defined in claim 13 wherein the head support member is width adjustable.

15. The apparatus as defined in claim 14 wherein the main support member is width adjustable.

16. The apparatus as defined in claim 13 wherein the head support member is movable toward and away from the main support member.

17. The apparatus as defined in claim 16 wherein the foot support member is movable toward and away from the main support member.

* * * * *